United States Patent [19]
Monson et al.

[11] Patent Number: 5,887,491
[45] Date of Patent: *Mar. 30, 1999

[54] SOIL ANALYSIS ASSEMBLY AND SYSTEM

[75] Inventors: Robert J. Monson, St. Paul; Norman A. Bauer, Watertown, both of Minn.

[73] Assignee: Ag-Chem Equipment, Co., Inc., Minnetonka, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 856,222

[22] Filed: May 14, 1997

[51] Int. Cl.$^6$ ........................................................ G01N 1/16
[52] U.S. Cl. ......................................... 74/864.74; 250/253
[58] Field of Search ............................ 73/864.81, 864.74, 73/864.73, 23.42, 864.44, 864.45; 111/118, 127, 904; 239/DIG. 15; 250/255, 253, 339.11, 339.1, 339.12; 356/402

[56] References Cited

U.S. PATENT DOCUMENTS

| | | | |
|---|---|---|---|
| Re. 35,100 | 11/1995 | Monson et al. | 111/130 |
| 3,464,504 | 9/1969 | Strange | 73/864.43 |
| 3,502,543 | 3/1970 | Sewell | 175/24 |
| 3,593,809 | 7/1971 | Derry | 175/51 |
| 4,266,878 | 5/1981 | Auer | 356/419 |
| 4,284,150 | 8/1981 | Davis | 175/84 |
| 4,332,301 | 6/1982 | Jonell | 175/50 |
| 4,333,541 | 6/1982 | Duty | 175/162 |
| 4,482,021 | 11/1984 | Repski | 175/209 |
| 4,630,773 | 12/1986 | Ortlip | 239/1 |
| 4,685,339 | 8/1987 | Philipenko | 73/864.45 |
| 4,828,047 | 5/1989 | Rogerson | 173/24 |
| 4,998,590 | 3/1991 | Wells | 175/162 |
| 5,033,397 | 7/1991 | Colburn, Jr. | 111/118 |
| 5,038,040 | 8/1991 | Funk et al. | 250/341 |
| 5,044,756 | 9/1991 | Gaultney et al. | 325/698 |
| 5,076,372 | 12/1991 | Hellbusch | 175/20 |
| 5,213,169 | 5/1993 | Heller | 175/122 |
| 5,298,139 | 3/1994 | Huang et al. | 204/299 |
| 5,310,462 | 5/1994 | Chen | 204/180.1 |
| 5,332,480 | 7/1994 | Datta et al. | 204/180.1 |
| 5,355,815 | 10/1994 | Monson | 111/200 |
| 5,366,601 | 11/1994 | Jones et al. | 204/180.1 |
| 5,453,924 | 9/1995 | Monson et al. | 364/131 |
| 5,461,229 | 10/1995 | Sauter et al. | 250/253 |
| 5,467,271 | 11/1995 | Abel et al. | 364/420 |
| 5,548,115 | 8/1996 | Ballard | 250/253 |
| 5,561,516 | 10/1996 | Noble et al. | 250/253 |
| 5,587,538 | 12/1996 | Bratton | 73/864.74 |

FOREIGN PATENT DOCUMENTS

| | | |
|---|---|---|
| WO95/04450 | 2/1995 | WIPO . |
| WO95/04870 | 2/1995 | WIPO . |
| WO96/04553 | 2/1996 | WIPO . |

OTHER PUBLICATIONS

New Tool Prescribes Precise Nitrogen Needs; Grant Mangold; *Soybean Digest* Feb. 1988.

Sensors Utilizing Light Reflection to Measure Soil Organic Matter; M. Pitts, J. Hummel, B. Butler; *American Society of Agricultural Engineers*, Jun. 1983.

(List continued on next page.)

*Primary Examiner*—Robert Raevis
*Attorney, Agent, or Firm*—Larkin, Hoffman, Daly & Lindgren, Ltd.

[57] ABSTRACT

The present invention relates to a soil anslysis system for determining various soil characteristics. Various soil characteristics may include moisture content, organic matter content and the presence of nitrogen phosphate, potassium and other elements. The soil analysis system includings a plurality of testing assemblies for determining soil characteristics. The soil analysis system further includes a soil testing device or probe which is operatively inserted into the soil to support the testing assemblies. Preferably, the soil analysis system is used in cooperation with a positioning system and a data collection system for recording soil characteristic data based upon the geographic location to which the soil characteristic data relates.

12 Claims, 15 Drawing Sheets

OTHER PUBLICATIONS

Undercover Light 'Reads' Soil Organic Level; *Successful Farming, Planning Issue* Nov., 1987.

Close–Range Sensing of Soil Organic Matter; P. Krishman, B. J. Butler, J. Hummel; *Transactions of the ASAE–1981*.

Spectroscopic Sensing for the Determination of Organic Matter Contest; J. Shonk, L. Gaultney; *American Society of Agricultural Engineers–Jun. 1988*.

Automated Nitrate Monitoring System; Nova Scotia Agricultural College, no date.

Test Your Soil for Acidity; College of Agriculture and Agricultural Experiment Station; Circular 346; C.M. Linsley and F.C. Bauer, no date.

Chromatography; Richard Villalobos, Beckman Instruments, Inc. (pp. 286–294), no date.

Reflection of Radiant Energy From Soils; Soil Science, vol. 100 No. 2; S.A. Bowers and R.J. Hanks, Aug. 1964.

Spectrophotometric Measurement of Soil Color and Its Relationship to Moisture and Organic Matter; J.A. Shields, E.A. Paul, R.J. Sr. Arnaud and W.K. Head, Apr. 1968.

Improved Soil Organic Matter Sensor with Microprocessor Control; Jeffrey Ruckman, John Hummel, B. Jack Butler; American Society of Agricultural Engineers, no date.

Color, Organic Matter, and Pesticide Adsorption Relationship in a Soil Landscape; R.N. Fernandez, D.G. Schulze, D.L. Coffin, and G.E. Van Scoyoc, Apr. 1987.

Biological and Physical Considerations in Applying Computer–Aided Analysis Techniques to Remote Sensor Data; Roger M. Hoffer; Remote Sensing: The Quantitative Approach Dec. 1978.

American Society of Agricultural Engineers; 001–2351/85, May/Jun. 1985, pp. 703–705.

Derivative Sensor, no date.

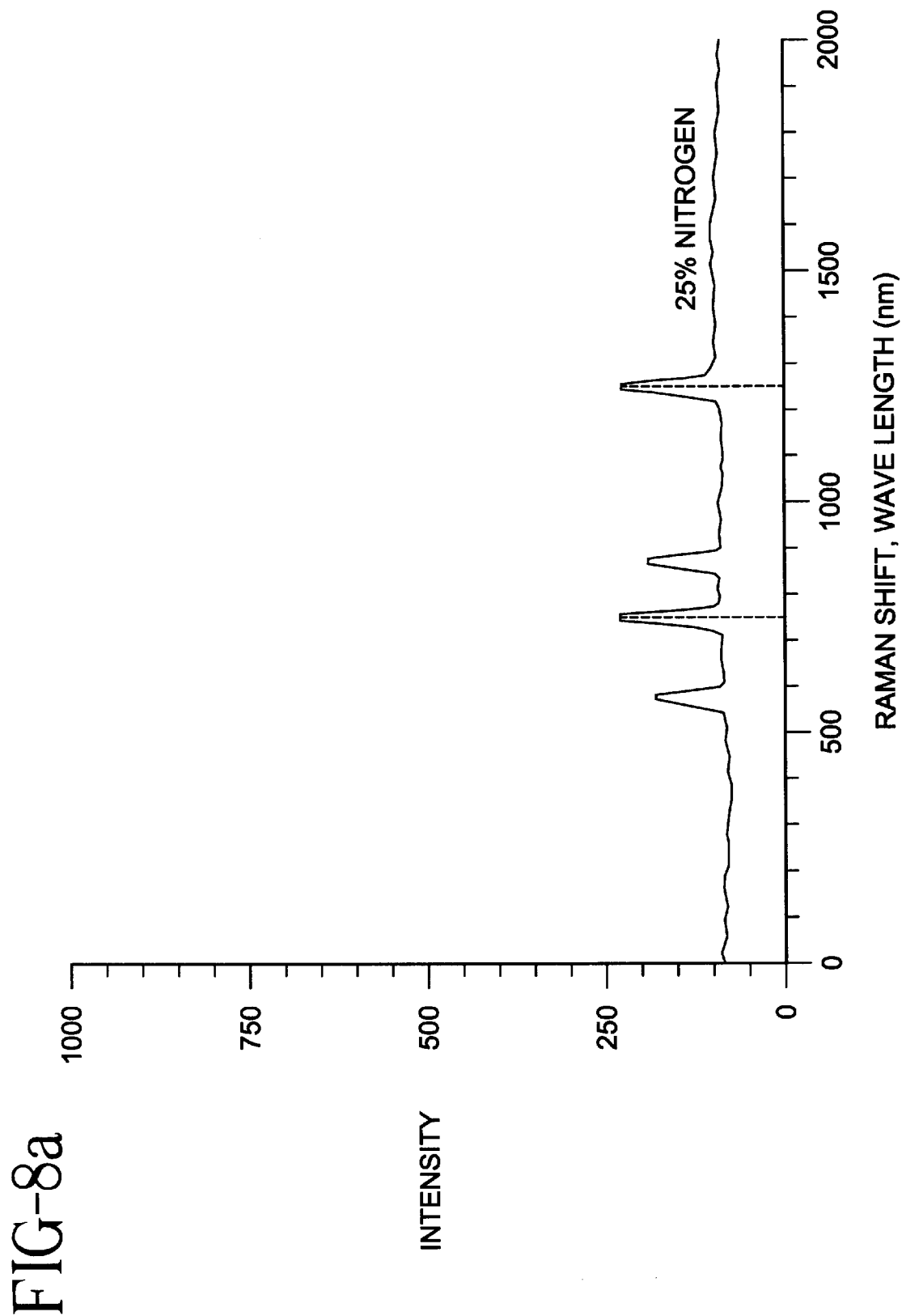

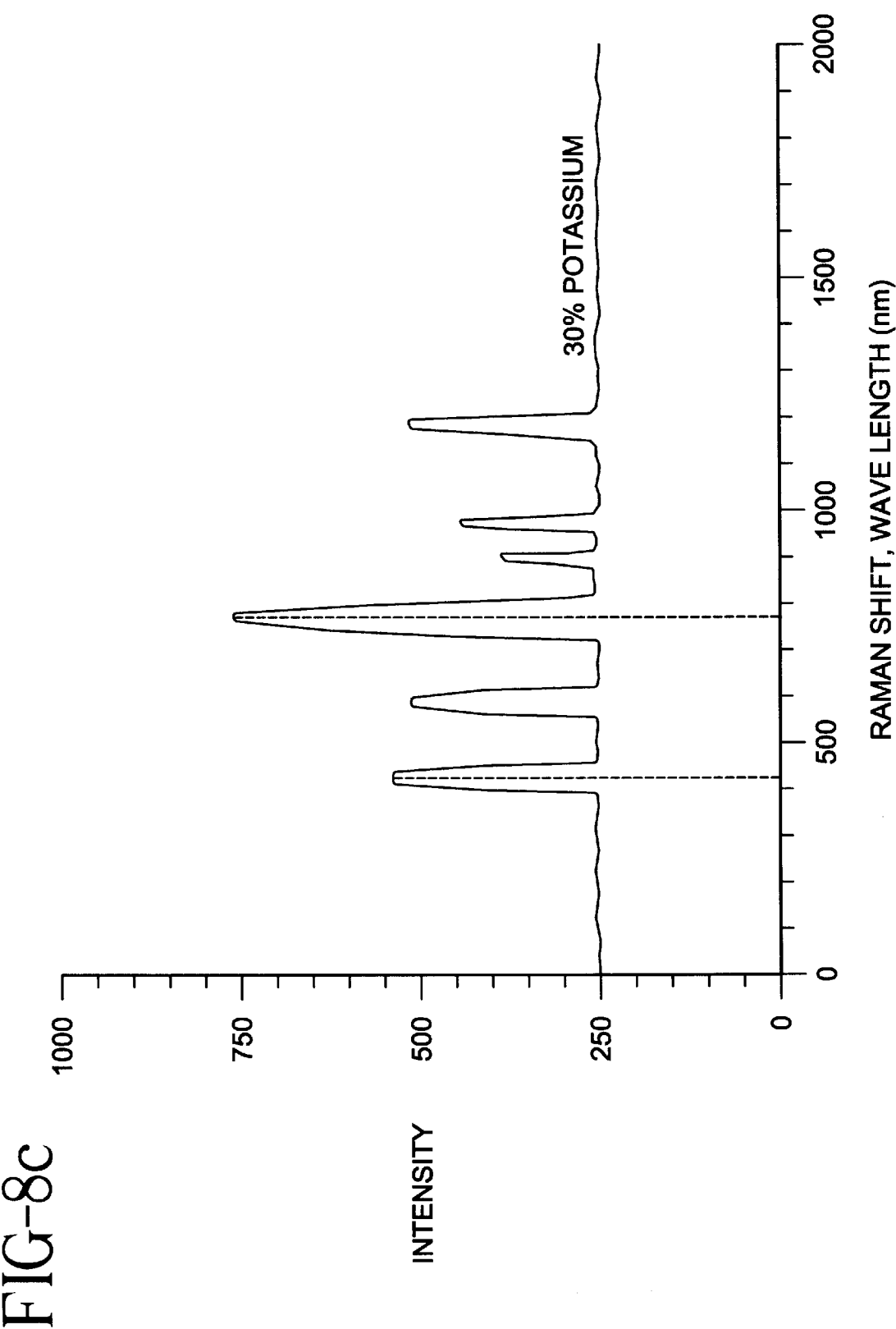

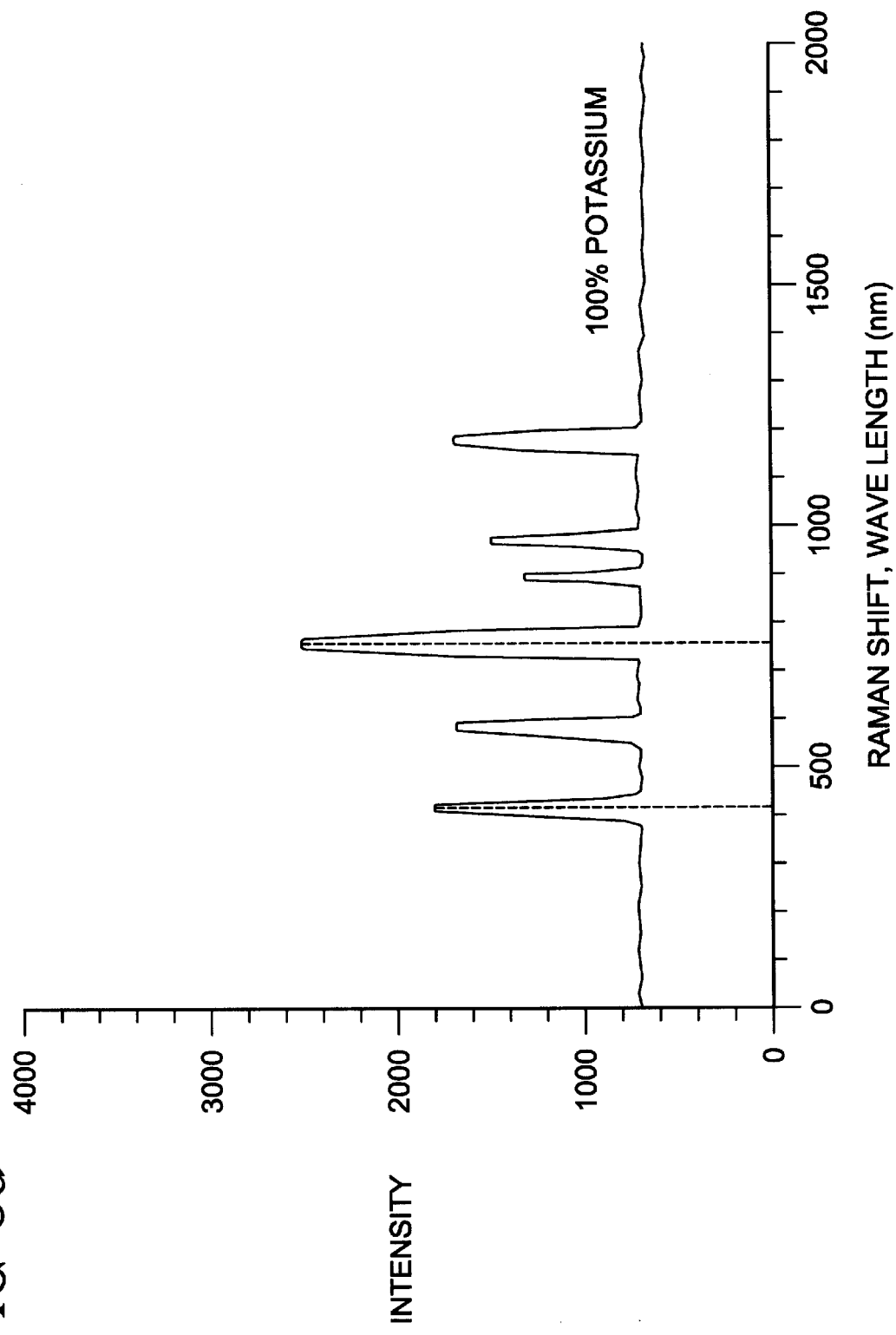

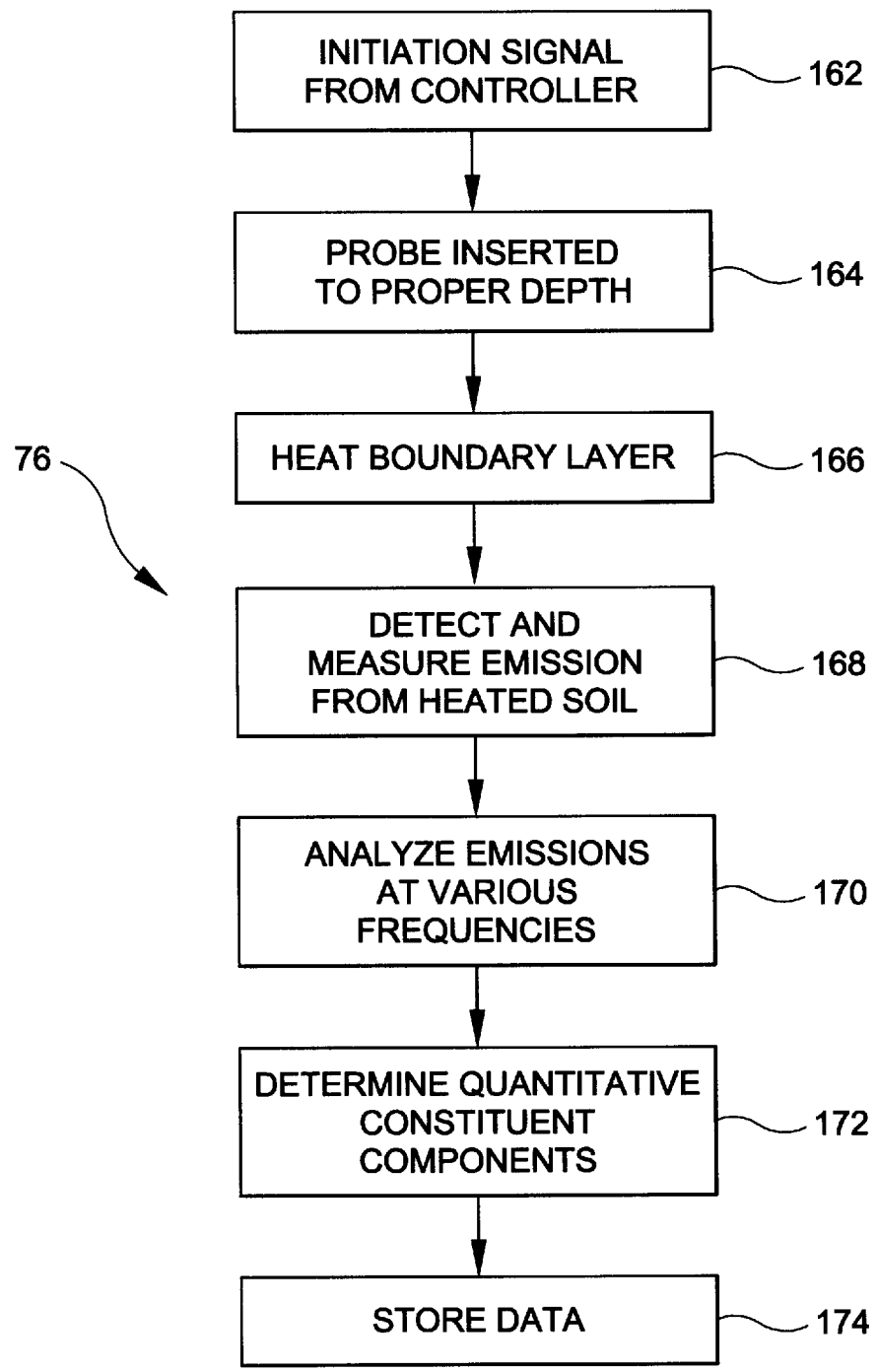

SOIL ANALYSIS ASSEMBLY AND SYSTEM

BACKGROUND OF THE INVENTION

The present invention relates to a soil analyzer. In particular, the present invention relates to a soil analyzer for analyzing soil characteristics.

Soil analysis techniques are utilized to determine certain soil characteristics for agricultural application. The soil of a field may be analyzed for purposes of selecting crop as well as analyzing application rates for fertilizer and other chemicals. Systems have developed for providing variable rate application of fertilizer and other products to a field. Different soil characteristics may affect the analysis for determining the proper quantity of a particular product to be applied to a field. It is desirable to provide a soil analysis system which provides the necessary data for effectively analyzing the quantity of product to be applied to a field. It is also desirable to have a soil analysis system which can be used to provide soil characteristic information by location in a field. Accordingly, different areas of a field may have different soil characteristic conditions, and it is desirable to provide a soil analysis system which creates a database of soil characteristics for different areas of a field.

SUMMARY OF THE INVENTION

The present invention relates to soil analysis system which includes a variety of testing assemblies for determining soil characteristics. As previously discussed, various soil characteristics affect the application of various products to a field. The present invention is designed to provide data regarding various soil characteristics so that each soil characteristic may be analyzed for the purpose of determining application of product. Preferably, the soil analysis system includes a soil contacting device which is used in combination with the testing assemblies, a data collection system, and a positioning system, such as a global positioning system which incorporates the use of satellites for determining geographic position. This data collection system is coupled to the testing assemblies and the positioning system to record soil characteristic data measured through the soil contacting device and the related geographic position of the soil sample which was measured.

BRIEF DESCRIPTION OF THE DRAWINGS

FIG. 8a is an illustrative graph of a spectra for nitrogen sensed by a spectrograph of a soil sample.

FIG. 8c is an illustrative graph of a spectra for potassium sensed by a spectrograph of a soil sample.

FIG. 8d is an illustrative graph of a reference spectra for a soil sample containing 100% potassium.

FIG. 9 is an operational diagram of operation of the thermal infrared reflectance testing assembly.

DETAILED DESCRIPTION OF THE PREFERRED EMBODIMENTS

Figure 1:
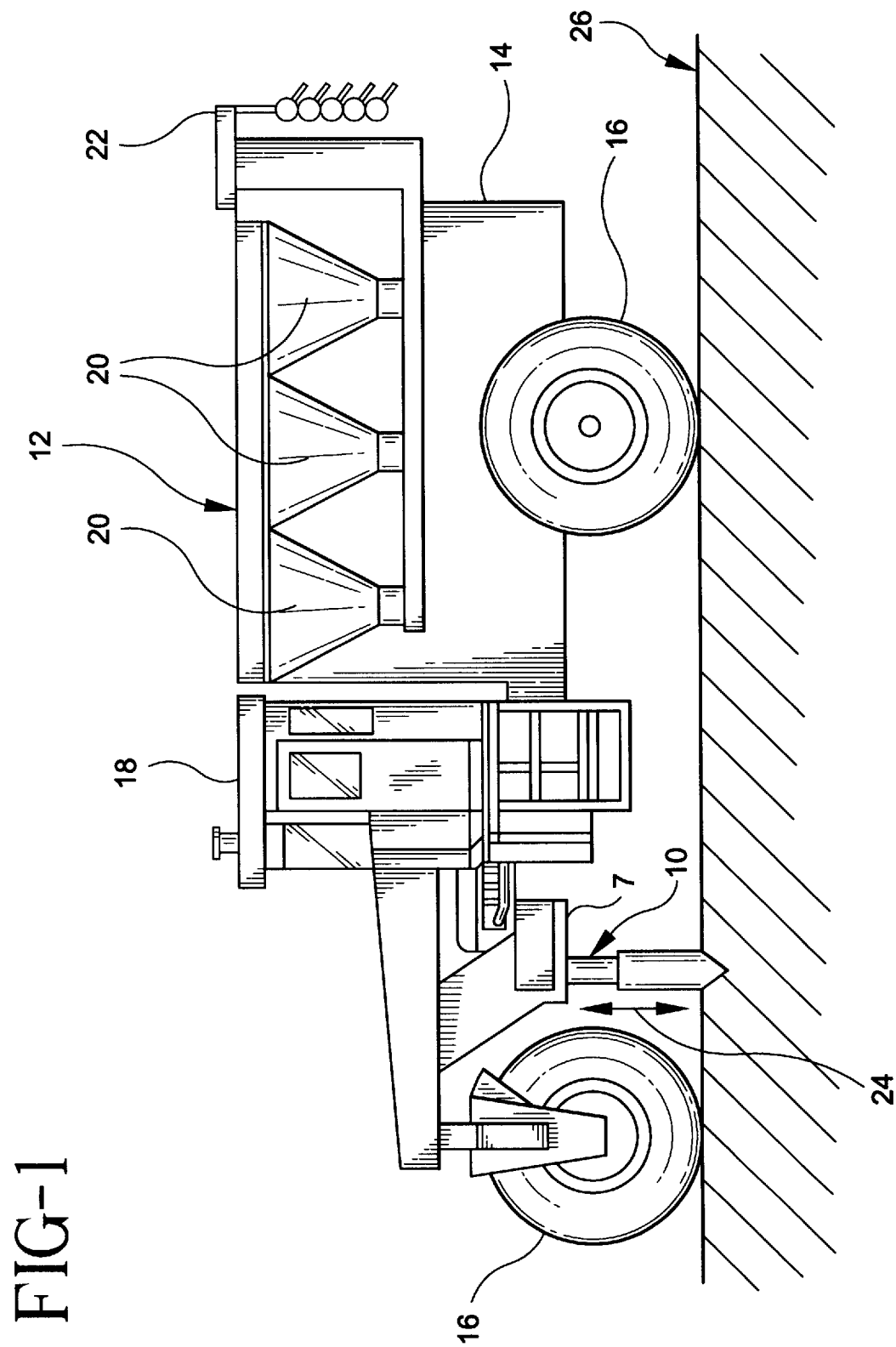
FIG. 1 is an elevational view of a vehicle incorporating a soil analysis system of the present invention.

The present invention relates to a soil analysis system 8 for ascertaining soil characteristics which affect plant or vegetation growth. In particular, the soil analysis system 8 of the present system is designed for "on-the go" collection of soil characteristic information for analysis. As shown in relation to FIG. 1, the soil analysis system 8 includes a soil contacting testing device 10 which may be coupled to a vehicle 12 for use. The vehicle 12 shown may be a dispensing vehicle or a testing vehicle and includes a frame 14, wheels 16 and cab 18. If the vehicle is used for dispensing materials, the vehicle may include dispensing hoppers 20 and a dispensing apparatus 22 for dispensing material from the hoppers 20. A dispensing controller (not shown) controls the dispensing rate of material from the dispensing apparatus 22 for dispensing material from hoppers 20.

As will be described in one embodiment of the invention, the dispensing controller may be coupled to the soil analysis system 8 to control the dispensing rate of material based upon the "output" of the soil analysis system 8. It should be recognized, however, that it is not necessary that the soil analysis system 8 be used in combination with a vehicle designed for dispensing material via a dispensing apparatus 22, but may be used with a testing vehicle for collecting soil characteristic data from a field for analysis.

Preferably, the soil contacting testing device 10 includes a formed soil insertion probe. The probe 10 is moveably supported relative to the frame 14 to move up and down as indicated by arrow 24 for insertion into the soil or ground 26 between an operational position and a non-operational position as will be described. The probe 10 of the present invention is a multi-function probe 10 which is designed to support a plurality of soil characteristic tests for analysis of a particular soil sample or region of interest. Accordingly, the multi-function probe 10 of the present invention supports a plurality of various characteristic tests for an accurate analysis of the characteristics of a region of interest.

Figure 2:
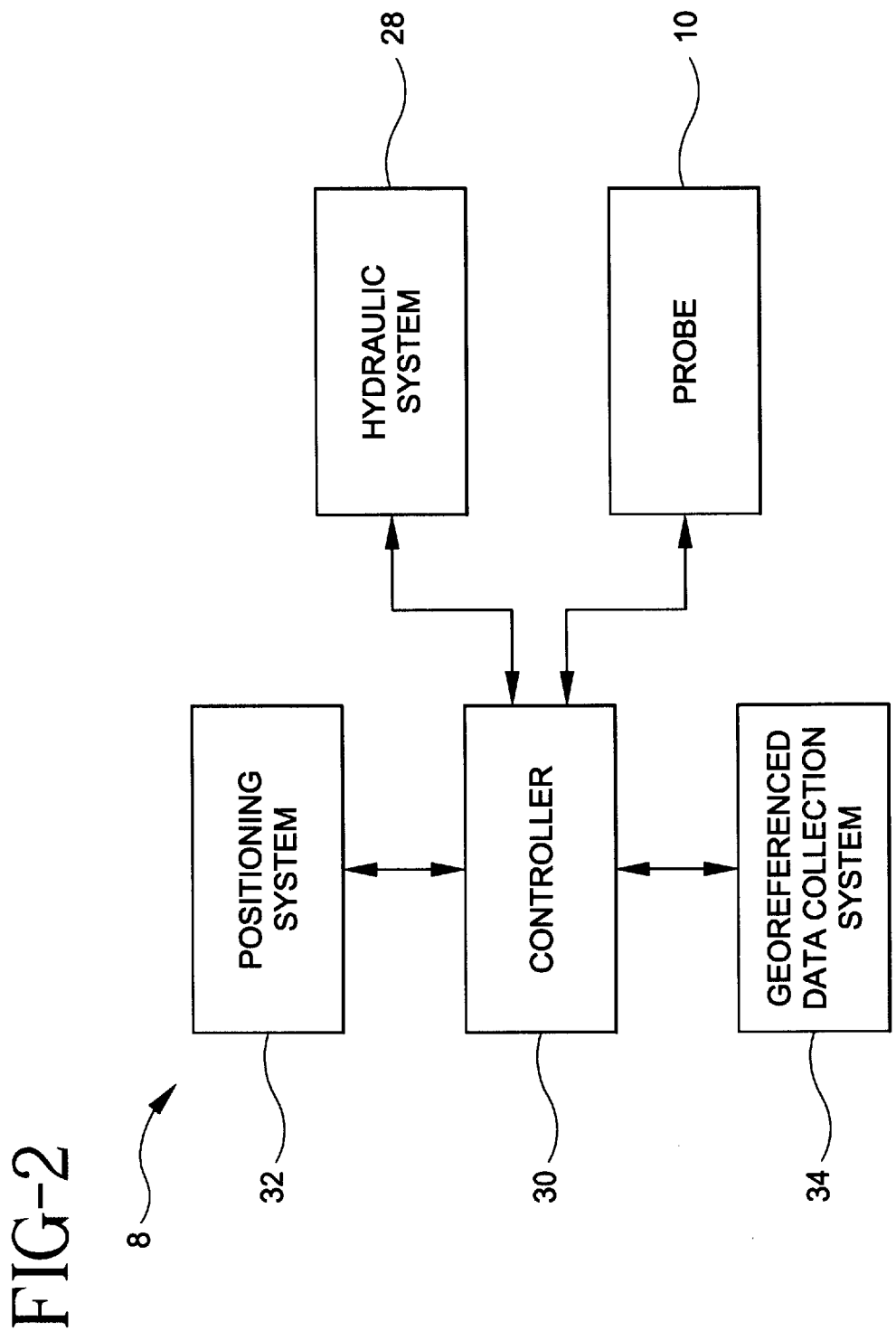
FIG. 2 is a block diagram illustrating operation of the probe of the present invention.

FIG. 2 is a schematic view illustrating components of a preferred embodiment of the soil analysis system 8 incorporating probe 10 of the present invention. As shown, the probe 10 is coupled to a hydraulic system 28 for raising and lowering the probe into the ground for operation. Preferably, the probe 10 and hydraulic system 28 are designed so that the probe 10 may be driven to an operational position below the soil surface for testing. A depth of 24 inches for the probe 10 tip is envisioned. Preferably, the probe 10 and hydraulic system 28 are designed so that the probe 10 may be retracted from the operational position to a non-operational position above the soil surface. Operation of the probe 10 and hydraulic system 28 is accomplished by a central controller 30. As shown in FIG. 2, the system 8 also includes a positioning system 32 and a data collection system 34. The positioning system 32 may be a system which is capable of correlating vehicle 12 position (i.e. probe position) relative to field location. Preferably, the positioning system 32 incorporates a global positioning system (GPS) which determines geographic position based upon a system of satellites.

The data collection system 34 stores data collected from the testing assemblies for possible subsequent analysis and evaluation. The collected data is referenced relative to the field location at which the data is collected. Preferably, the collected data is georeferenced and is stored relative to the geographic latitude and longitude coordinates for the field position at which the data is collected. The controller 30 initiates operation of the hydraulic system 28 for operating the probe 10 at selected locations based upon a predetermined pattern. The positioning system 32 provides position data to the controller 30 for positioning the probe 10 for operation at the selected locations. Data collected from the probe 10 is then stored by the data collection system 34 relative to field location based upon information from the positioning system 32.

Figure 3:
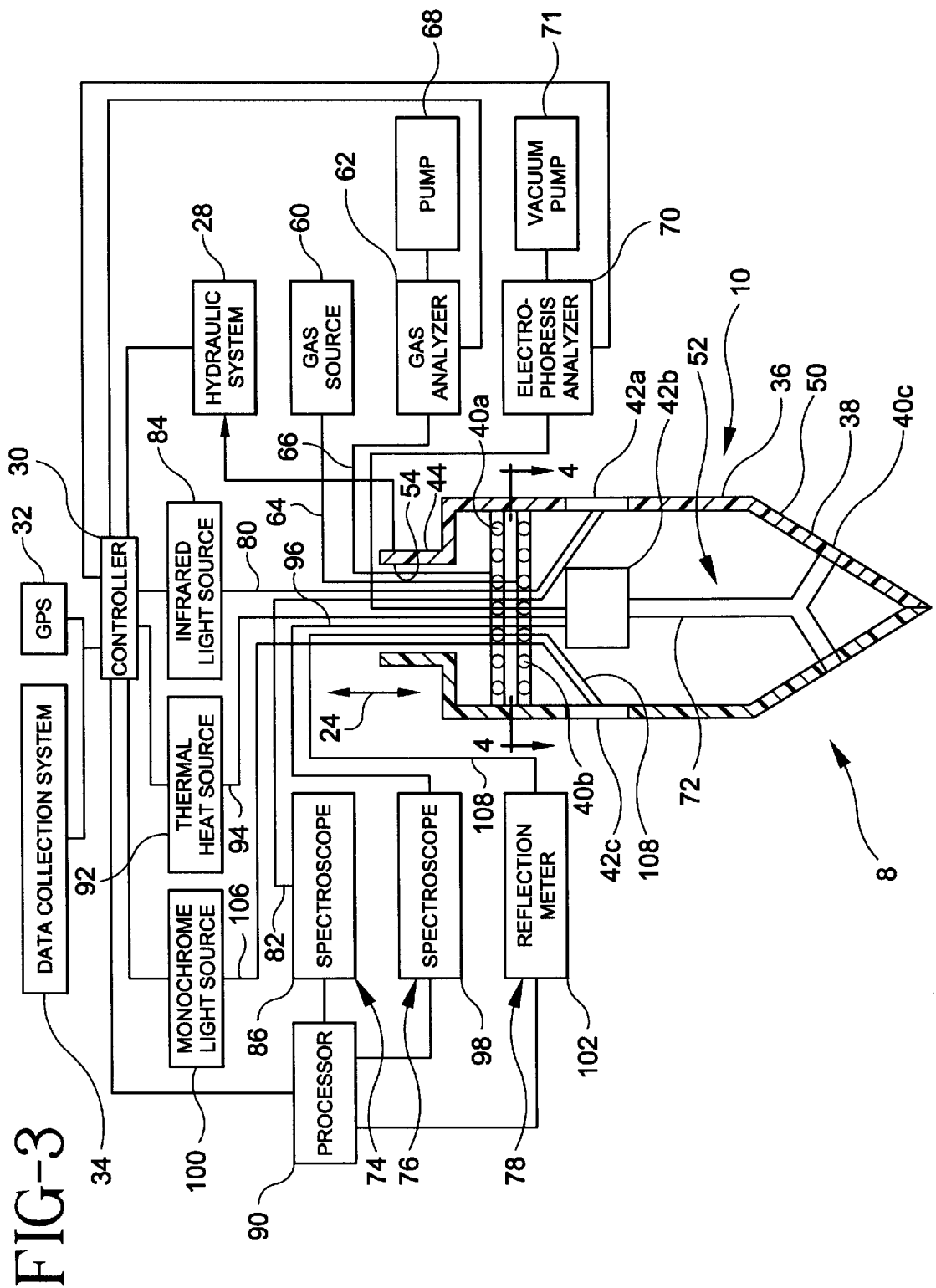
FIG. 3 is a cross-sectional view of the probe schematically illustrating operation of the testing assemblies of the probe.

FIG. 3 is a cross sectional view of probe 10 illustrating components of the probe 10 in schematic form. The probe 10 of the present invention is capable of supporting a multitude of tests for evaluation of the productivity potential of various field locations. The probe 10 is essentially a cylindrically shaped member 36 having a conical tip 38 to facilitate insertion of the probe 10 into the ground 26. As shown in FIG. 3, the probe 10 includes a plurality of holes 40a–c, which extend about an outer circumference of the probe as will be described further herein and a plurality of windows 42a–c extending about an outer perimeter of the probe 10. These form the components of the multiple testing assemblies of the probe 10 of the present invention.

As shown in FIG. 3, the probe 10 is moveably supported for insertion into the ground via a rod 44 fixedly coupled to an upper end of the probe 10 and moveably coupled relative to a base 7 by the hydraulic system 28 to move as illustrated by arrow 24. The cylindrically shaped member 36 and conical tip 38 of the probe 10 are constructed of an outer housing 50 having a hollow interior defining an inner compartment 52. The rod 44 connecting the probe 10 relative to a vehicle or other support is a hollow elongated member defining an inner conduit 54.

In a preferred embodiment, the probe 10 supports various testing assemblies including reflectance testing assemblies, an electrophoresis testing assembly, and a chromatography testing assembly. The chromatology testing, reflectance testing and electrophoresis testing are used to isolate elements or minerals found in the soil and to analyze various soil characteristics.

Various reflectance testing assemblies may be used for the purpose of analyzing moisture content, organic matter content as well as mineral composition of a soil sample. It is generally known that reflectance characteristics of the soil relate to soil texture, moisture content, surface roughness, iron oxide content and organic matter content. Additionally, certain nutrients have unique reflectance characteristics and produce a unique spectral image which allows the content of these nutrients to be analyzed for a particular soil sample. It is desirable to use a combination of tests for comparison for evaluating the influence of the various factors affecting reflectance for the purpose of isolating soil characteristics relating to moisture content, organic matter content and nutrient content. The results of the combination of testing assemblies may be used to provide a more accurate determination of soil characteristics. Although it is preferred to use multiple testing assemblies for determining soil characteristics, it should be understood that it is not necessary that each of the testing assemblies described be employed and the invention should only be limited by the claims appended hereto.

Figure 4:
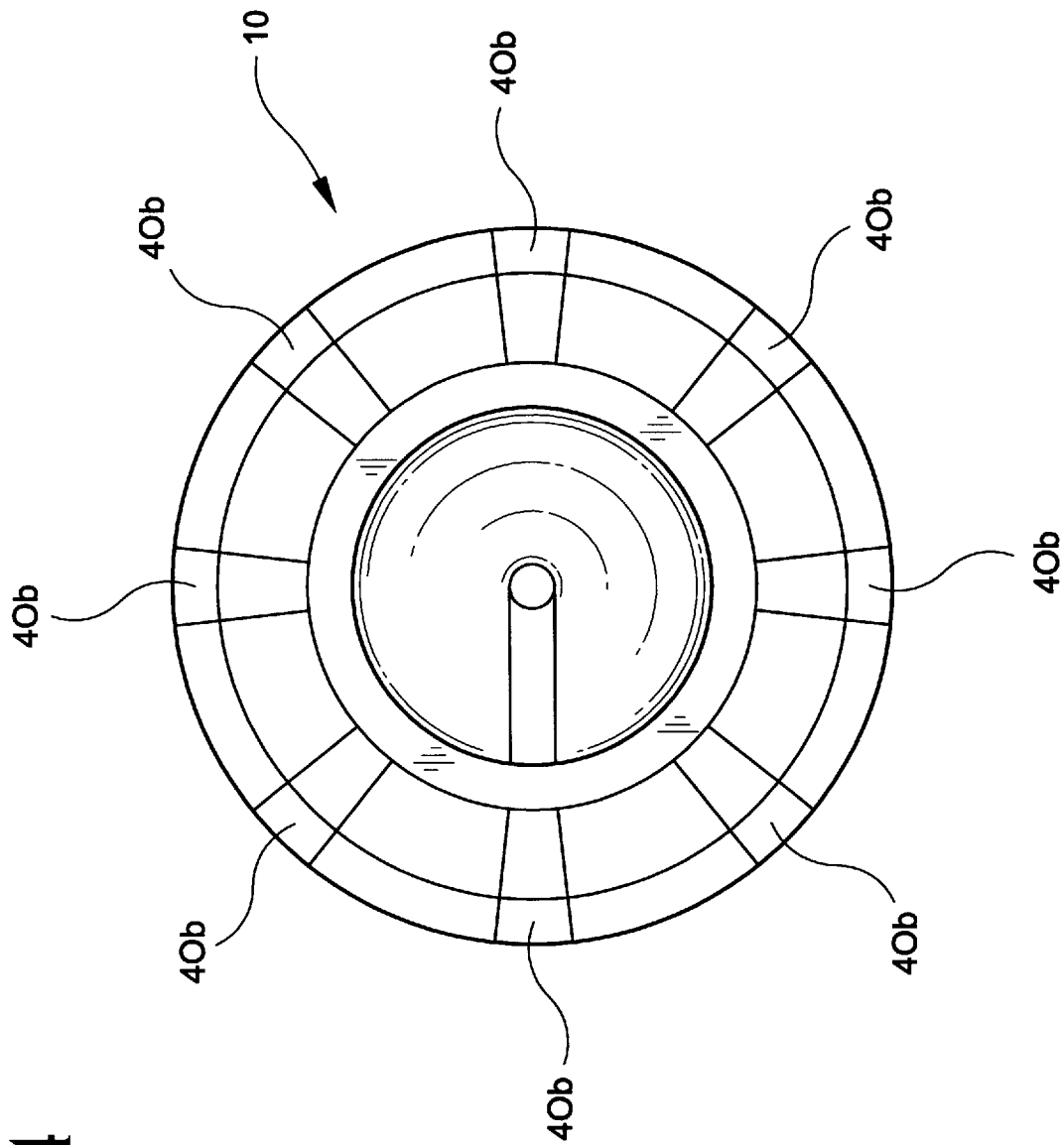
FIG. 4 is a cross-sectional view of the probe taken along line 4—4 of FIG. 3.

Preferably, the holes 40a–c of the probe 10 are used to extract physical soil samples for analysis and the windows 42a–c are used to collect reflectance data from a soil sample. In particular, physical samples are extracted for chromatography and electrophoresis testing. As shown in FIGS. 3 and 4, holes 40a–b are used for chromatography testing and holes 40c are used for electrophoresis testing. A chromatography testing assembly includes a gas source 60 and a chromatography analyzer assembly 62 shown schematically. Preferably, the gas source 60 and chromatography analyzer assembly 62 are supported by the vehicle 12. The gas source 60 is coupled to holes 40b of probe 10, through a conduit 64 shown schematically. The conduit 64 extends through the inner conduit 54 of the rod 44 into probe 10 to connect the plurality of spaced holes 40b extending about the circumference of the probe 10 for introducing a gas solution for chromatography analysis.

Similarly, holes 40a include a plurality of spaced holes which are spaced upwardly of holes 40b and are coupled to a conduit 66 shown schematically. The conduit 66 is coupled to holes 40b and extends through inner conduit 54 of rod 44. The conduit 66 is coupled to the chromatography gas analyzer 62. Thus, gas flows from the gas source 60 through holes 40b for introducing a buffer gas into the soil sample. A sample of the gaseous soil is extracted through holes 40a for analysis by the gas analyzer 62 via pump 68 for analyzing a soil sample as will be described.

The electrophoresis testing assembly includes a capillary tube electrophoresis analyzer 70, a pump 71 and conduit 72. Preferably, the electrophoresis analyzer 70 and pump 71 are supported by vehicle 12. Conduit 72 is coupled between holes 40c and the electrophoresis analyzer 70 for extracting soil samples for analysis through holes 40c. Soil samples are extracted through conduit 72 which extends through rod 44 and probe 10 via pump 71.

As shown in FIG. 3, the probe 10 supports three separate reflectance testing assemblies 74, 76 and 78. The reflectance testing assembly 74 may be used to determine moisture and nutrient content and includes optical cables 80 and 82, an infrared light source 84, a spectroscope unit 86. Optical cable 80 is coupled between the infrared light source 84 and window 42a to provide infrared light to a soil sample. Optical cable 82 is coupled between window 42a and the spectroscope unit 86. The reflected light from the soil sample is detected by the spectroscope unit 86 via optical cable 82. The reflectance at various wavelengths is analyzed for the purpose of analyzing different attributes of the soil sample. Different attributes of the soil sample are analyzed via a processing assembly 90 to determine the content of nitrogen, potassium, phosphorus and other elements as will be described herein. The soil characteristic data such as the content of nitrogen, etc. is stored in the data collection system 34 based upon the geographic location of the soil sample as determined by the global positioning system 32.

The reflecting testing assembly 76 is similar to assembly 74 except that the testing assembly 76 measures infrared thermal reflectivity. The testing assembly 76 is used in combination with data from reflectance assembly 74 to provide accurate measurements of moisture content and nutrient content. The reflectance testing assembly 76 includes a thermal heat source 92, a thermal cable 94, an optical cable 96 and a spectroscope unit 98. The thermal heat source 92 is used to heat a boundary layer of a soil sample via the thermal cable 94. The cable is coupled between the thermal heat source 92 and window 42b of the probe 10. Optical cable 96 is coupled between the window 42b and spectroscope unit 98 to measure the spectral reflectance of the excited soil sample. The spectral reflectance is similarly separated to analyze the reflectance at various wavelengths. Different attributes of the soil sample are analyzed via the processing assembly 90. The thermal energy source 92 may be gas, a heated paten, or a UV or incandescent lamp.

The reflectance testing assembly 78 is used to isolate organic matter content as taught by U.S. Pat. No. 5,044,756. The assembly 78 includes a monochrome light source 100, a reflection meter 102 for measuring the reflectance from the soil and optical cables 106 and 108 for transmitting the monochrome light source to the soil sample and for transmitting reflected light to the reflection meter 102. Optical cable 106 is coupled between the light source 100 and window 42c to illuminate a soil sample. Optical cable 108 is coupled between window 42c and reflection meter 102 to measure light reflected by the illuminated soil sample. Preferably, the monochrome light source 100 is red or yellow light. It has been found that the reflectance of red or yellow light is more accurately related to organic matter content since factors such as iron oxides can be reduced. Data from the assembly 78 is combined by the processing assembly 90 with other spectral reflectance data to eliminate certain variables affecting the reflectance measurement so that the reflectance affecting organic matter content can be evaluated to determine soil organic matter content.

Windows 42a–c are preferably formed of a Plexiglas material to separate the inner compartment 52 of the probe 10 from the soil and allow light to pass through the windows 42a–c to analyze reflectance while protecting the components of the probe. Operation of testing assemblies of the probe 10 is controlled via controller 30. Data from the testing assemblies is stored via location by the data collection system 34. Data is stored via location in cooperation with the GPS positioning system 32. Although embodiments of the reflectance testing assemblies have been described having operational components such as illumination sources and measuring devices supported on a vehicle, it is not intended that the invention be limited to such a configuration.

Figure 5:
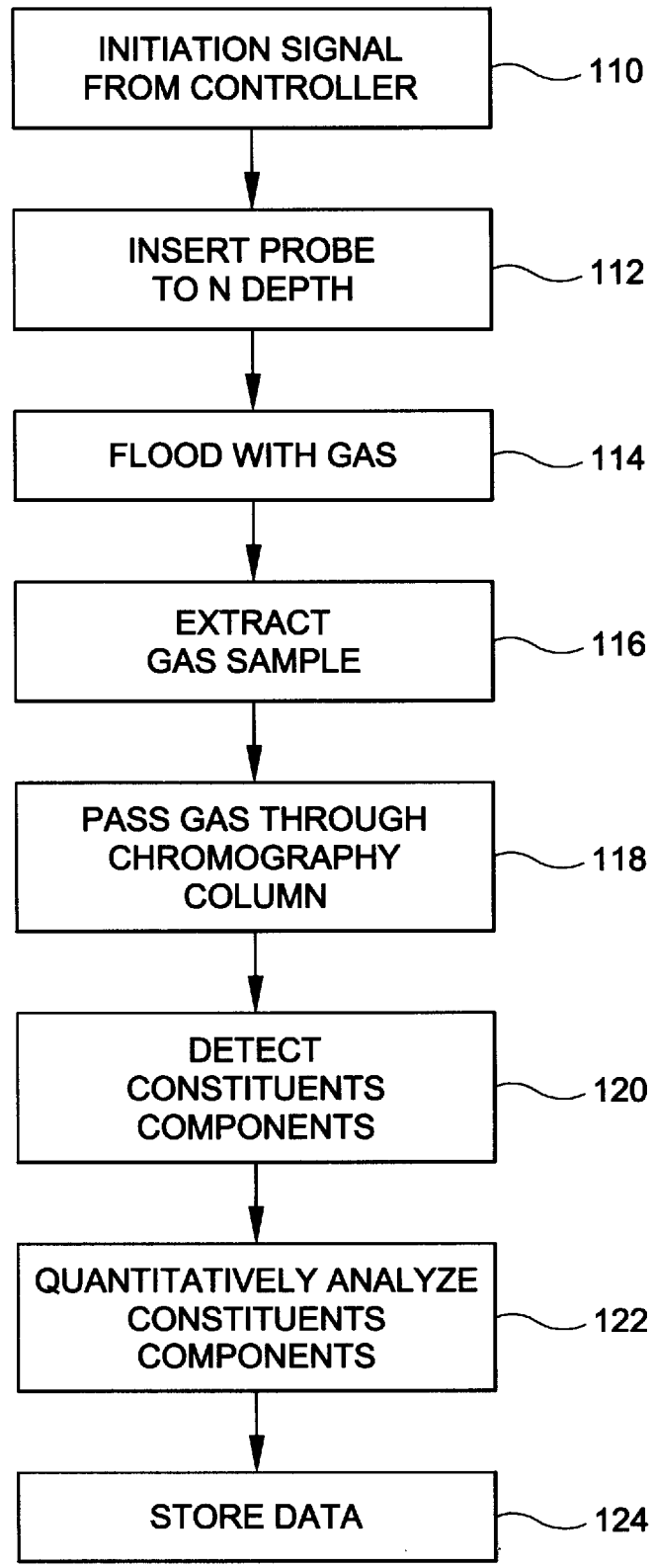
FIG. 5 is an operational diagram of operation of the chromatography testing assembly.

FIG. 5 is a block diagram illustrating operation of the gas chromatography testing assembly. Operation of the chromatography testing assembly is controlled by initiation from the controller 30 as illustrated block 110. The controller 30 operates the hydraulic system 28 to insert the probe 10 into the ground as illustrated in block 112. As illustrated by block 114 after the probe 10 is positioned, a carrier gas from gas source 60 is pumped into the soil through conduit 64 coupled to hole 40b. The carrier gas may be any gas which will not interfere with detection of elements of the sample, such as helium, hydrogen or argon. A vacuum source 72 is used to extract the carrier gas from the soil via holes 40a and conduit 66 for analysis as illustrated by block 116. When the carrier gas is extracted it will contain components which will be detected from the gas chromatography analyzer 62. The gas chromatography analyzer 62 is an "on-line" column for separating different components of the soil sample via absorption rates. A detector is coupled to the column to measure components of the separated soil sample. The sample extracted is continuously passed through the "on-line" column where different components of the sample are separated and detected by a detector as illustrated by blocks 118–120. The data from the detector is converted into quantitative composition data 122. This data is stored via operation of the controller 30 and the positioning system 32 by the data collection system 34 as illustrated by block 124.

Figure 6:
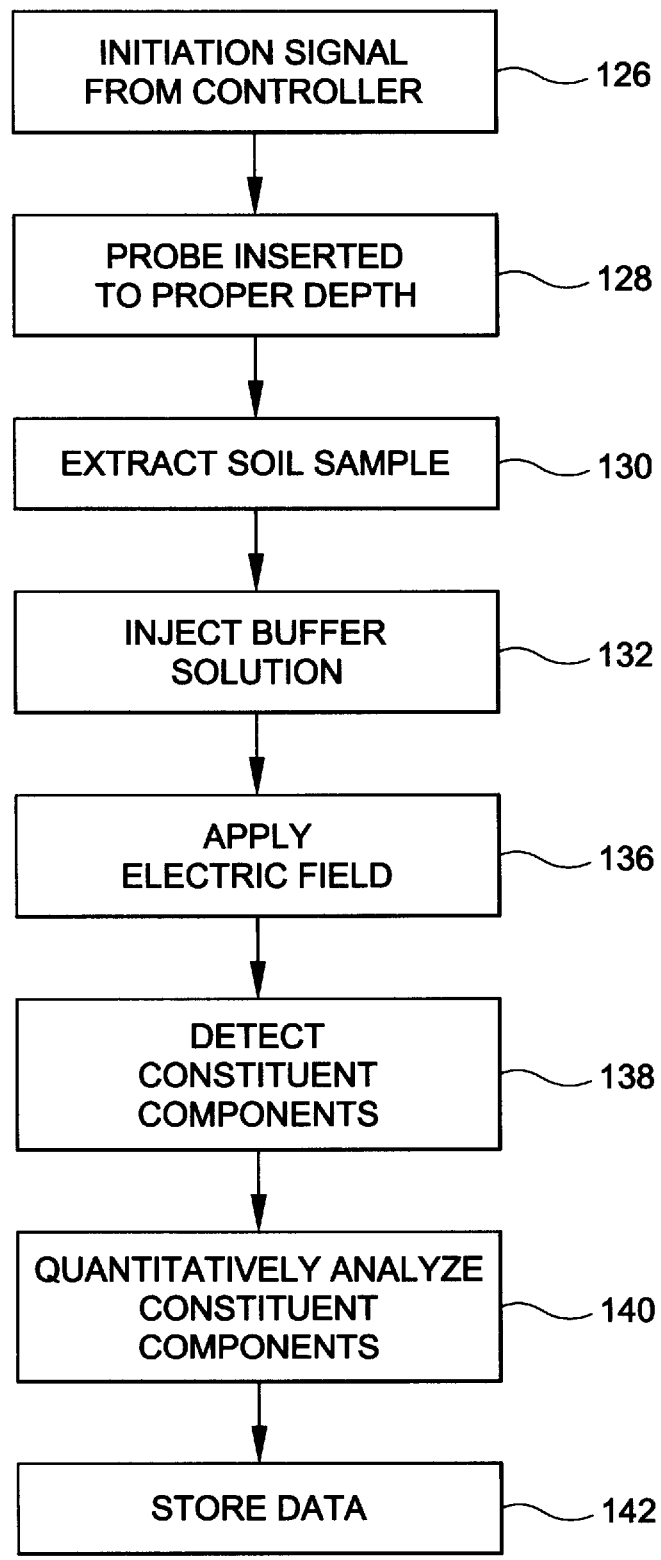
FIG. 6 is an operational diagram of operation of the electrophoresis testing assembly.

FIG. 6 is a block diagram illustrating operation of the electrophoresis testing assembly. Similar to operation described for the gas chromatography testing assembly, operation is initiated by controller 30 as illustrated by blocks 126–128. A soil sample is extract via the probe 10 as illustrated by block 130. The soil sample is extracted through holes 40c and conduit 72 via a vacuum source 71. The sample is put into a capillary tube (not shown) and a ph buffer solution is injected into the soil sample as illustrated by block 132. An electric field is applied to the sample in the thin capillary tube to separate the particles of interest as illustrated by block 136. Since different particles or elements have different electric charge potential and the particles or elements migrate at different rates towards a charge potential the elements separate for detection when an electric field is applied.

A detector is used to measure the amount of various particles or elements present at different charge potentials as illustrated by block 138. The detector may employ a device which detects the absorption/reflectance of light at different wavelengths at various locations along the capillary tube to isolate the amounts of various particles or elements. Results of the detector are used to establish quantitative measurements of various constituent components of the soil sample as illustrated at block 140. This testing assembly may be used to detect levels of nitrogen or other elements in the field. The results of the detection process are analyzed and recorded based upon geographic location and stored in the data collection system 34 as illustrated by block 142.

The capillary tube used must be cleaned after each test cycle so that the residue of the previous test does not interfere with the next test. After each testing cycle, the test capillary tube is flushed with a cleaning solution to prepare the capillary tube for reuse. If test samples are taken and need to be analyzed fairly rapidly, such as "on-board" a testing vehicle which is moving through a field, then a plurality of testing tubes are employed so that sequential test samples may be taken and analyzed for various field locations without waiting for the prior test to be completed. A controller (not shown) is employed to assign sequential test tube stations for rapid collection of data as a testing vehicle moves through a field. After a test tube is cleaned and prepared for reuse, a signal is sent back to the machine controller to indicate that the test tube stations are ready for use. The number of test tube stations depends upon the time interval at which the samples are to be taken at various field locations.

Figure 7:
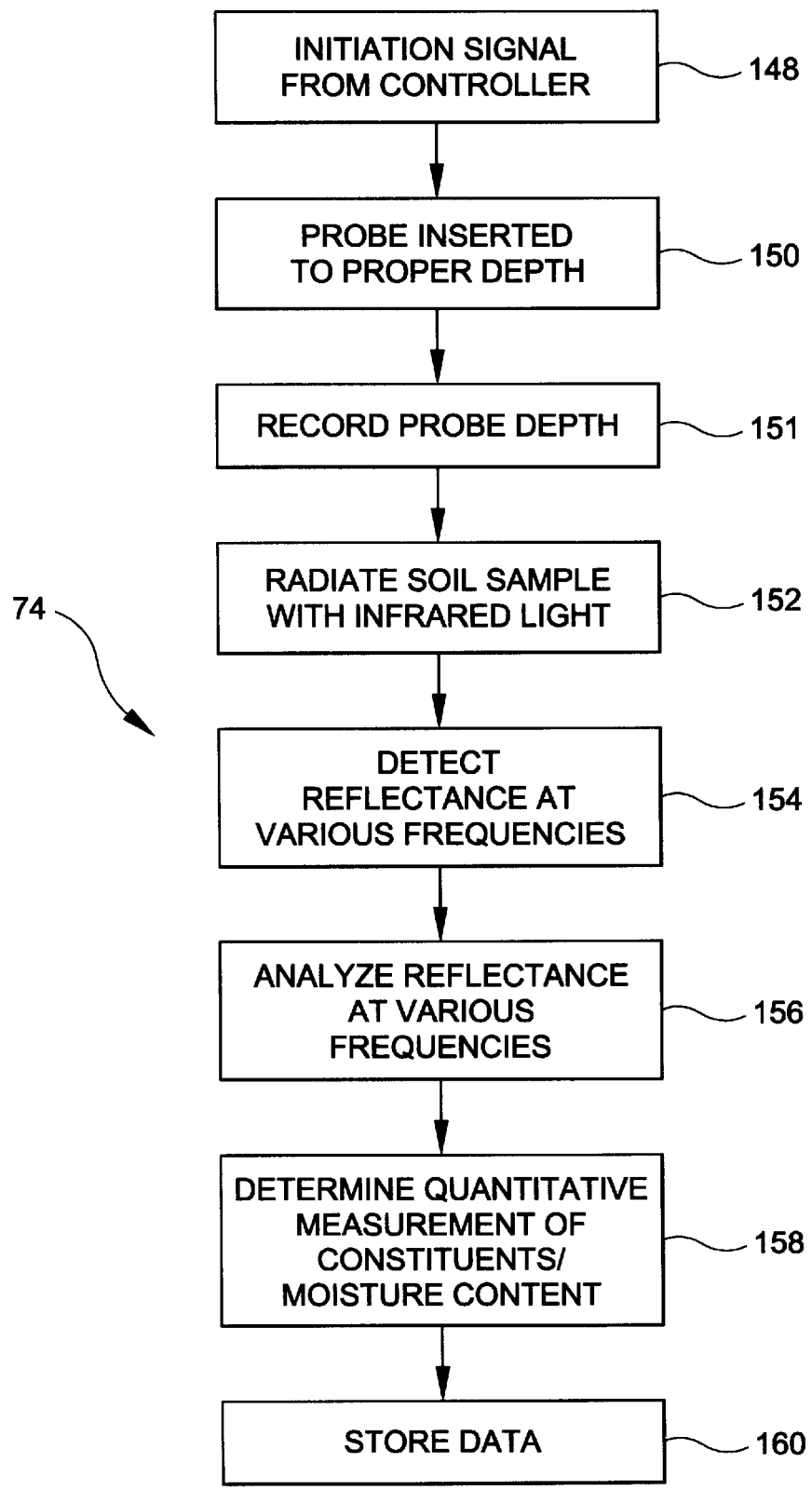
FIG. 7 is an operational diagram of operation of a reflectance testing assembly.

FIG. 7 is a block diagram illustrating operation of the reflectance testing assembly 74 which may be used to distinguish elements, such as nitrogen, potassium, phosphorous and zinc. After the probe 10 is initiated by the controller 30, as illustrated by blocks 148–150. The depth of the inserted probe 10 is recorded as illustrated at block 151. A soil sample is radiated with light from an infrared light source 84 as illustrated by block 152. The reflectance of the soil sample for various frequencies is detected via a spectrograph and analyzed as illustrated by blocks 154 and 156. Different elements of interest are excited at different frequencies. For example, potassium will optimally fluoresce when excited by a 766 nm wavelength, nitrogen at 1246.9 nm, phosphorous at 956.3 nm and zinc at 636.2 nm. The various wavelengths at which each of the elements radiates or peaks is unique and the intensities of the peaks are dependent upon the illumination source. Due to quantum mechanics, each element will produce a unique spectral image for a given illumination source, allowing the spectral images to be distinguished as shown in FIGS. 8a–8f.

Figure 8B:
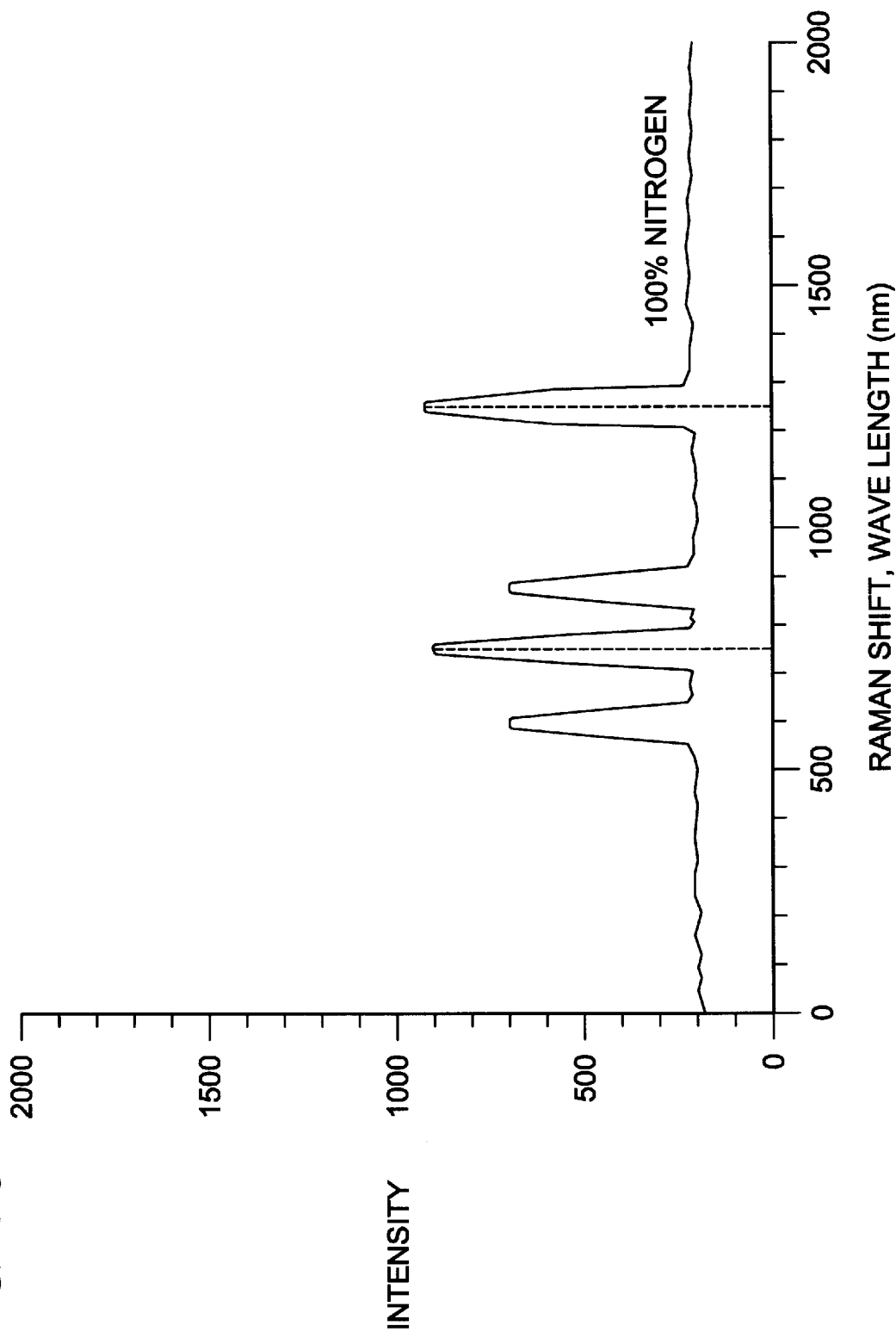
FIG. 8b is an illustrative graph of a reference spectra for a soil sample containing 100% nitrogen.
Figure 8E:
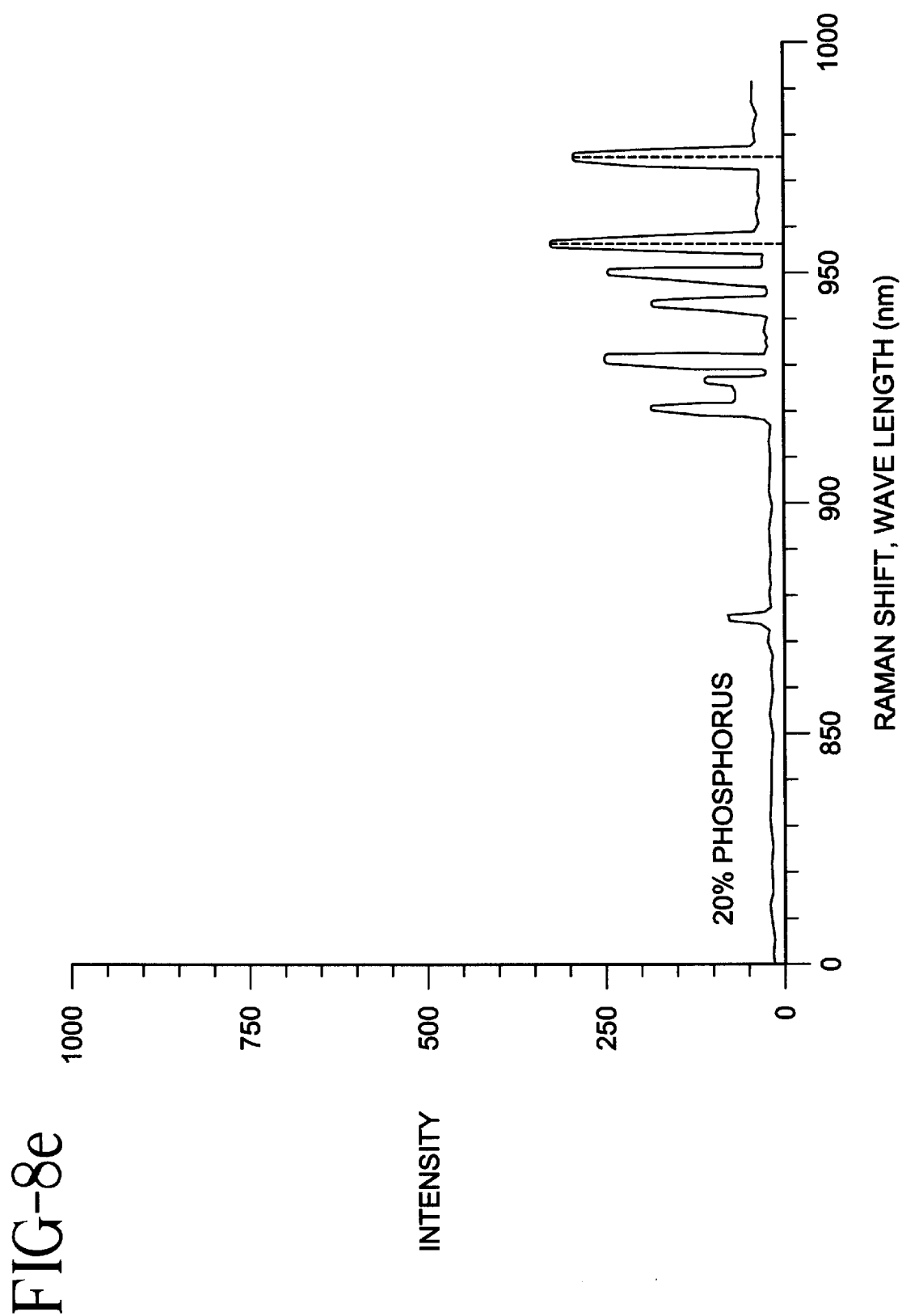
FIG. 8e is an illustrative graph of a spectra for phosphorus sensed by a spectrograph of a soil sample.
Figure 8F:
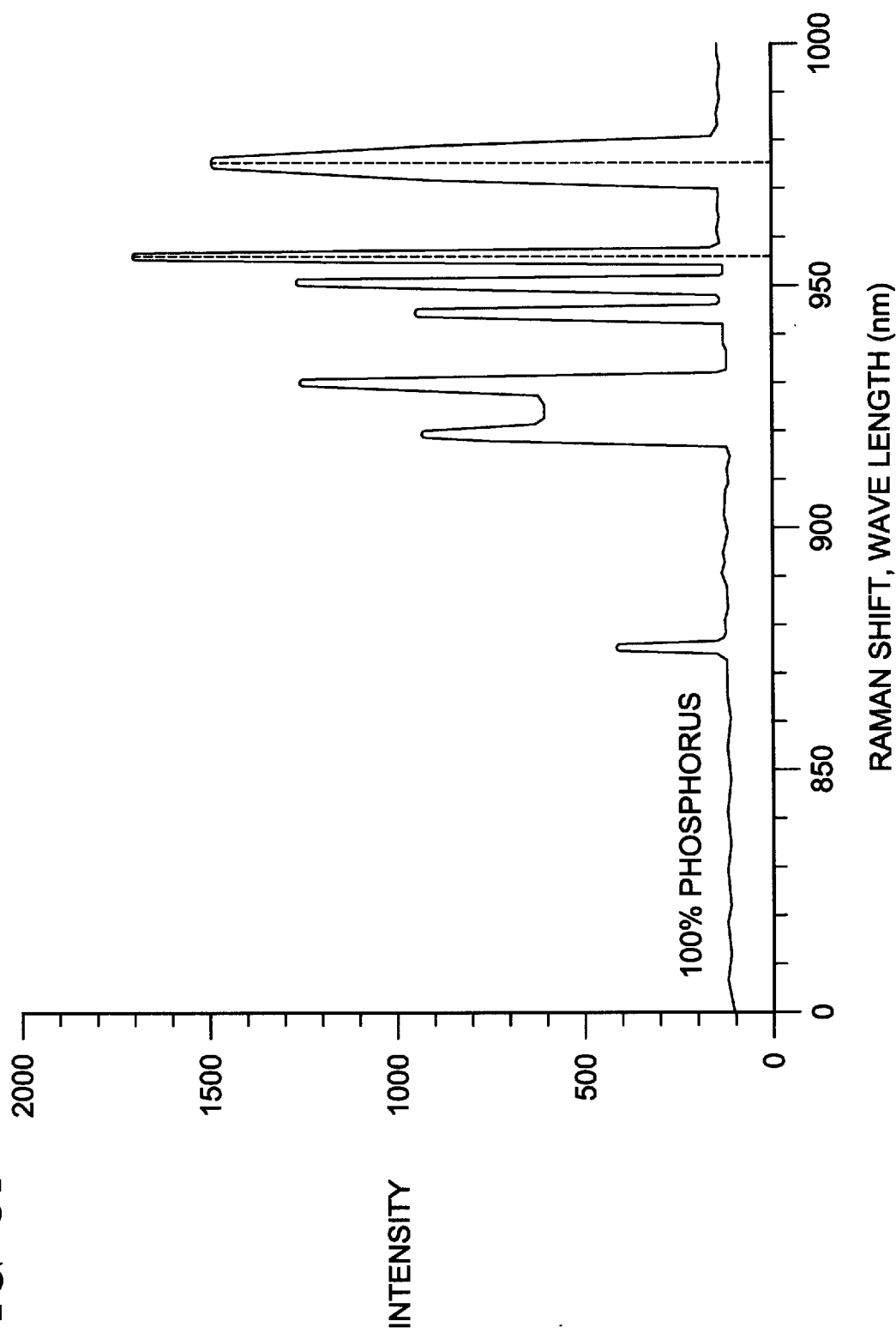
FIG. 8f is an illustrative graph of a reference spectra for a soil sample containing 100% phosphorus.

Spectral data for each of the elements tested is stored for comparison with the measured reflectance by the processing assembly 90. The spectral data includes the spectral image for 100% of the interested elements, such as nitrogen, potassium, phosphorous and zinc as shown in FIGS. 8b, 8d and 8f. These images are compared with the tested images as shown in FIGS. 8a, 8c and 8e for determining the percentage of nitrogen, potassium, phosphorous or zinc in the test sample as described in U.S. Pat. No. 5,355,815 incorporated herein by reference to determine the percentage composition of each of the elements of interest in the soil sample as illustrated by block 158. The system also analyzes the quantity of infrared reflection for analyzing moisture content based upon stored comparison data. The system also records the depth of the probe 10 at block 151 since soil depth may affect moisture content. The system includes known data for correlating reflectance at selected infrared frequencies to analyze soil moisture content. The measured reflectance is converted into soil moisture content data in a known manner. After, the percentage of each of the interested elements is determined the data is stored by location in the data collection system 34 as illustrated by block 160. The soil moisture content data (including moisture content and soil depth) is stored by location by the collection system 34.

FIG. 9 is a block diagram illustrating operation of the thermal infrared reflectance assembly 76 for analyzing the presence of certain chemicals or elements in a soil sample, such as potassium, nitrogen and phosphorus. This assembly 76 is similar to the infrared reflectance testing assembly, except that a thin layer of the soil is heated and reflectance of the heated soil is measured. The testing assembly 76 uses a heat source 92 such as a heating coil which heats a boundary layer of a soil sample adjacent to the window 42b. The window 42b is formed of a material with sufficient heat conductivity. Operation of the thermal infrared reflectance assembly 76 is initiated via controller 30 which inserts the probe 10 into the ground 26 as illustrated by blocks 162 and 164.

The soil is heated to excite a boundary layer portion of the soil for analysis as illustrated by block 166. The emission from the heated boundary layer of the soil is detected and measured at selected frequencies as illustrated by block 168. The emission at various wavelengths is analyzed and compared with known emission data of various elements to determine the composition of the soil as illustrated by blocks 170 and 172 in a known manner. Data relating to the composition of the soil is stored by location by the data collection system 34 as illustrated by block 174. The elevated temperature may range from 4 degrees Celsius or 150 degrees Celsius above ambient as illustrated in U.S. Pat. No. 5,461,229.

Figure 10:
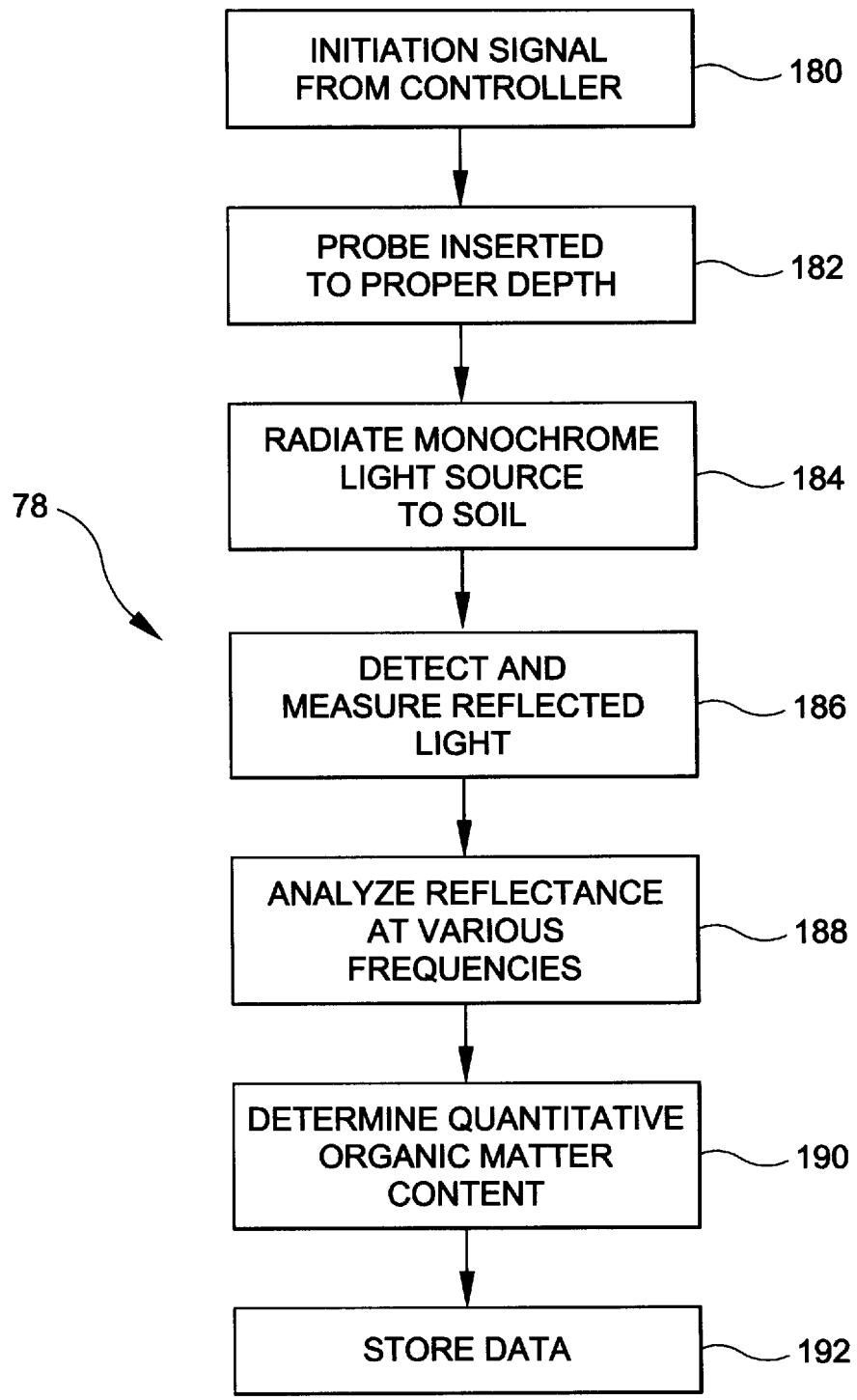
FIG. 10 is an operational diagram of operation of a monochrome reflectance testing assembly.

FIG. 10 is a block diagram illustrating operation of the monochrome reflectance testing assembly 78 for use in measuring organic matter content. The magnitude of reflected light from a monochromatic light source is generally related to texture, moisture content, surface roughness, iron oxide content and organic matter content. Thus, to the extent other variable can be eliminated, the relative organic matter content of the soil at different locations can be analyzed. Iron oxides typically absorb light in the visible and infrared wavelengths, except for some areas in the yellow and red regions, thus, the monochromatic light source is preferably, a red light source to eliminate the influence of iron oxides.

As shown in FIG. 10, operation of the reflectance testing assembly 78 is initiated by the controller 30 and the probe 10 is inserted into the ground 26 as illustrated by blocks 180 and 182. As illustrated by block 184, a monochromatic light (preferably red) source is supplied to a soil sample. The magnitude of reflected light is measured as illustrated by block 186. The reflected light is analyzed based upon known equations and data of the system as illustrated by block 188 in a known manner as generally described in U.S. Pat. No. 5,044,756 as incorporated herein by reference to determine organic matter content as illustrated by block 190. As previously explained the magnitude of reflectance from the red light source is related to moisture content, texture and organic matter content.

Additional data, including data from other testing assemblies can be used to correlate data to determine organic matter content. For example, the relative particle size (or soil texture) may be measured or inputted to the system prior to operation. Depending upon the particle size of the soil, different equations are used to analyze organic matter content from the reflectance data. Additionally, soil moisture data may be used to factor in moisture content for the reflectance data to isolate the influence of moisture content on the reflectance data to isolate the organic matter content. Thus, a relative organic matter content may be derived for the soil sample which may be used for determining proper field treatments for maximum yield or performance. The relative organic matter content is stored by location by the data collection system 34 to build a database of field characteristics for various field locations for use in treating a field as illustrated by block 192.

While the present invention has been described above in connection with particular embodiments and examples, one skilled in the art will appreciate that the invention is not necessarily so limited. It will thus be understood that numerous other embodiments, examples, uses, modifications of and departures from the teachings disclosed may be made without departing from the scope and spirit of the present invention, and the scope of the present invention shall be limited with respect to the claims appended hereto.

What is claimed is:

1. A soil analysis system comprising:

a soil testing device adapted for intermittent contact with the soil and including a plurality of functionally different testing assemblies including: (1) one or more reflectance testing assemblies adapted for determination of moisture content, nutrient content, and organic matter content in a soil sample; (2) an electrophoresis testing assembly adapted for determination of the amount of particles or elements in a soil sample; and (3) a chromatography testing assembly adapted for detection of elements in a soil sample, the soil testing device adapted to be disposed in the soil at one or more geographic locations in a soil region and perform at least one test on the soil and provide associated soil characteristics relating to the soil obtained at the one or more geographic locations;

a data collection system adapted to store information relative to the associated soil characteristics and the one or more geographic locations; and a control system operably coupled to control operation of the soil testing device and the data collection system.

2. The soil analysis system of claim 1 wherein the soil analysis system includes a soil testing assembly for determining soil mineral composition.

3. The soil analysis system of claim 1 wherein the soil analysis system includes a testing assembly for determining soil moisture content.

4. The soil analysis system of claim 3 wherein the soil analysis system includes a testing assembly for determining organic matter content.

5. The soil analysis system of claim 1 wherein the soil testing device includes at least one window for radiating the soil and detecting reflection of said radiation from the soil for imaging the soil.

6. The soil analysis system of claim 1 wherein the soil testing device includes at least one opening for extracting a soil sample for analysis.

7. The soil analysis system of claim 6 wherein the soil testing device includes at least one opening for introducing a testing solution into a soil sample.

8. The soil analysis system of claim 1 and further comprising:

means for moveably supporting the soil testing device relative to a base between an operational position and a non-operational position; and means for selectively moving the soil testing device between the non-operational position and the operational position for testing the soil.

9. The soil analysis system of claim 1 wherein the soil analysis system includes a separation testing assembly for separating and detecting constituent components of a soil sample.

10. The soil analysis system of claim 1 further comprising:

a positioning system operably associated with the control system and the data collection system, the soil analysis system adapted to determine at least one geographic position within a geographic area containing a certain soil characteristic.

11. The soil analysis system of claim 1 further comprising:

a dispensing system including a controller coupled to the soil analysis system to control the dispensing rate of a product based upon a determination made by the soil analysis system.

12. A process for analyzing soil comprising:

positioning a vehicle at a first location in a soil region, the vehicle adapted to support at least a first and a second testing assembly for acquiring respective soil characteristic information using functionally different operations;

using the first testing assembly to acquire the first soil-characteristic information associated with the first location according to a first operation;

using the second testing assembly to acquire the second soil characteristic information associated with the first location according to a second operation;

combining the first soil-characteristic information and the second soil-characteristic information to provide composite soil-characteristic information;

determining a dispensing rate for a product based upon the composite soil-characteristic data associated with the first location; and dispensing the product at the dispensing rate about the first location.

* * * * *